United States Patent [19]

Kaufman et al.

[11] Patent Number: 5,589,348

[45] Date of Patent: Dec. 31, 1996

[54] IN SITU NICOTINAMIDE COENZYME GENERATING SYSTEM FOR ENZYME BASED CLINICAL CHEMISTRY ASSAYS

[75] Inventors: Richard A. Kaufman, Belleville; John M. Konopka, Westfield; Henry J. Rosenfeld, Florham Park; Janine E. Sabo, Lodi, all of N.J.

[73] Assignee: Hoffmann-La Roche Inc., Nutley, N.J.

[21] Appl. No.: 216,231

[22] Filed: Mar. 22, 1994

Related U.S. Application Data

[63] Continuation of Ser. No. 67,415, May 25, 1993, abandoned, which is a continuation of Ser. No. 930,494, Aug. 14, 1992, abandoned, which is a continuation of Ser. No. 800,654, Nov. 27, 1991, abandoned, which is a continuation of Ser. No. 447,337, Dec. 7, 1989, abandoned, which is a continuation-in-part of Ser. No. 399,052, Aug. 28, 1989, abandoned.

[51] Int. Cl.$^6$ .............................. C12Q 1/32; C12P 17/02
[52] U.S. Cl. .............................. 435/26; 435/123
[58] Field of Search .............................. 435/26, 123

[56] References Cited

U.S. PATENT DOCUMENTS

| | | | |
|---|---|---|---|
| 3,929,581 | 12/1975 | da Fonsera Wollheim | 435/26 |
| 3,974,037 | 8/1976 | Adams | 435/26 |
| 4,019,961 | 4/1977 | Klose et al. | 435/26 |
| 4,271,264 | 6/1981 | Modrovich | 435/26 |
| 4,394,449 | 7/1983 | Modrovich | 435/188 |
| 4,587,216 | 5/1986 | Patel et al. | 435/26 |
| 4,668,699 | 5/1987 | Hoffman et al. | 514/460 |
| 4,766,071 | 8/1988 | Simon et al. | 435/90 |
| 5,037,738 | 8/1991 | Lamos et al. | 435/12 |
| 5,116,728 | 5/1992 | Crowther et al. | 435/14 |
| 5,227,296 | 7/1993 | Goux | 435/110 |

FOREIGN PATENT DOCUMENTS

| | | |
|---|---|---|
| 2232760 | 6/1974 | France. |
| 2521591 | 2/1983 | France. |

OTHER PUBLICATIONS

Saked et al. (1980) *J. Am. Chem. Soc.*, 102, 7105–7107.
Wong et al. (1981) *J. Am. Chem. Soc.*, 103 (16), 4890–4899.
Crans et al. (1983) *J. Org. Chem*, 48, 3130–3132.
Lee et al. (1985) *J. Am. Chem. Soc.*, 107(24), 6999–7008.
Menson, et al., Clinical Chemistry, 20: 872 (Jul. 1974).
Wilson, et al., Clinical Chemistry, 19: 640 (1973).
Norris, et al., Clinical Chemistry, 21: 1093–1101 (1975).
H. C. van Anken, et al., Clinica Chimica Acta., 56: 151–157 (1974).
Walsh (1980) *Accts. Chem. Res.*, 13, 148–155.
Benkovic (1978) *Accts. Chem. Res.*, 11, 314–320.
Benkovic (1980) *Ann. Rev. Biochem.*, 49, 227–251.

*Primary Examiner*—John W. Rollins
*Assistant Examiner*—Jon P. Weber
*Attorney, Agent, or Firm*—George W. Johnston; Patricia S. Rocha-Tramaloni; Raina Semionow

[57] ABSTRACT

The invention relates to an improved enzymatic method for determining the concentration of an analyte in a sample body fluid. The improvement comprises a coupled enzyme reaction scheme comprising the in situ generation of reduced nicotinamide coenzyme, with either simultaneous or subsequent re-oxidation of coenzyme by an analyte substrate and substrate specific enzymes. The change in absorbance due to the reoxidation of coenzyme is proportional to the concentration of analyte in the reaction mixture.

27 Claims, No Drawings

IN SITU NICOTINAMIDE COENZYME GENERATING SYSTEM FOR ENZYME BASED CLINICAL CHEMISTRY ASSAYS

This is a continuation division of application Ser. No. 08/067,415, filed May 25, 1993, now abandoned which is a Rule 62 continuation of 07/930,494, filed Aug. 14, 1992, now abandoned; which is a Rule 62 Continuation of Ser. No. 7/800,654, filed Nov. 27, 1991 now abandoned; which is a Rule 60 Continuation of 07/447,337, filed Dec. 7, 1989, now abandoned; which is a CIP of 07/399,052, filed Aug. 28, 1989, now abandoned.

TECHNICAL FIELD

The instant invention provides an improved enzymatic method for determining the concentration of analyte in a sample body fluid which improvement comprises measuring the change in absorbance due to the re-oxidation of reduced coenzyme which is generated in situ. The change in absorbance is proportional to the concentration of analyte in the sample. The invention also provides methods for determining total $CO_2$ and ammonia using the method of the invention, as well as all of the novel reagents used in these methods, and diagnostic test kits useful for the determination of total $CO_2$ and ammonia in sample body fluids.

BACKGROUND OF THE INVENTION

The quantitation of analytes in sample body fluids by enzymatic methods is a fairly recent phenomenon. The basic procedure involves determining the sample "blank" by mixing a sample containing the analyte with the enzyme substrates known to be used for the quantitation of that particular analyte. Substrate specific enzymes are then added to the reaction mixture. The enzymatic conversion of the substrates and analyte results in a change in the reaction composition which can be quantitated by various methods which measure the change in absorbance due to the action of substrate specific enzymes on the substrates. This change in absorbance is then correlated with the concentration of analyte in the sample.

For example, the enzymatic quantitation of total $CO_2$ in serum or plasma involves mixing a sample containing $CO_2$ with the substrate phosphoenolpyruvate (PEP). After a blank reading is taken, the substrate specific enzyme phosphoenolpyruvate carboxylase (PEPC) is added causing the conversion of PEP to oxaloacetate (OAA) and phosphate according to the following reaction:

$$PEP + CO_2 \xrightarrow[MG^{2+}]{PEPC} OAA + P_i$$

The OAA produced is then correlated with the concentration of $CO_2$ in the sample by various methods. For example, in Wilson et al., *Clinical Chemistry*, 19:640 (1973) and Munson et al., *Clinical Chemistry*, 20:872 (1974), both of which are hereby incorporated by reference, the OAA is simultaneously coupled with reduced nicotinamide adenine dinucleotide (NADH) and malate dehydrogenase (MDH) such that the amount of NADH oxidized is directly proportional to the $CO_2$ in sample. In Norris, et al., *Clinical Chemistry*, 21:8, 1093 (1975), also incorporated by reference, the OAA is quantitated by reaction with the diazonium salt of Fast Violet B. One principle disadvantage of enzymatic methods for $CO_2$ is that they are very sensitive to interference from atmospheric $CO_2$, especially at the alkaline pH required for optimum reaction and stability of NADH.

Plasma ammonia may also be determined enzymatically according to the method of Van Anken et al., *Clinical Chemica Acta*, 56:151 (1974) which is also incorporated by reference. This method is based upon the following reaction:

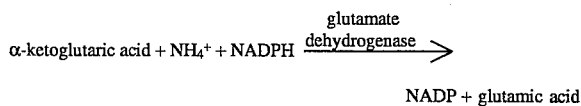

$$\alpha\text{-ketoglutaric acid} + NH_4^+ + NADPH \xrightarrow{\text{glutamate dehydrogenase}} NADP + \text{glutamic acid}$$

The NADP produced is proportional to the concentration of ammonia in the sample and may be quantitated by measuring the change in absorbance due to the oxidation of the coenzyme NADPH to $NADP^+$.

The enzymatic reagents in this method are also very unstable, particularly the coenzyme NADPH.

SUMMARY OF THE INVENTION

The instant invention comprises an improvement to those enzymatic methods which determine the concentration of an analyte in a sample body fluid by measuring the change in absorbance due to the action of substrate specific enzymes on a sample-substrate reaction mixture, which improvement comprises measuring the change in absorbance due to the re-oxidation of a reduced coenzyme generated in situ after the addition of substrate specific enzymes to sample-substrate reaction mixture to which the coenzyme has been added. This invention is applicable to the determination of a variety of analytes such as $CO_2$, ammonia, Aspartate Transaminase (AST), Alanine Transaminase (ALT), Lactic Dehydrogenase (LDH, pyruvate to lactate), Triglyceride, salicylate, and urea.

The instant invention also comprises a method for determining total $CO_2$ in a sample body fluid according to this improved method, including the novel reagent compositions used as well as a diagnostic test kit useful for the determination of total $CO_2$ in a sample.

The instant invention also comprises a method for determining ammonia concentration in a sample body fluid according to this improved method, including the novel reagent compositions used as well as a diagnostic test kit useful for the determination of ammonia in a sample.

DETAILED DESCRIPTION

The coenzymes preferably used in the method of the invention are nicotinamide adenine dinucleotide (NAD) and nicotinamide adenine dinucleotide phosphate (NADP), although coenzyme analogs such as nicotinamide hypoxanthine dinucleotide phosphate or thio-NAD would also be suitable. The preferred substrate/enzyme system for generating the reduced coenzyme is the glucose-6-phosphate (G6P)/glucose-6-phosphate dehydrogenase (G6PD) system, although many other substrate/enzyme systems such as glucose/glucose dehydrogenase and formate/formate dehydrogenase may also be used. G6P is added to the sample-substrate reaction mixture along with the coenzyme and enzyme substrates used for quantitation of the particular analyte of interest. A first absorbance reading comprising the sample blank is taken. The substrate specific enzymes are then added. An alternative procedure would involve addition of sample subsequent to the in situ production of reduced coenzyme resulting from mixing substrate specific enzymes and the appropriate substrates and coenzyme, with the initial absorbance reading taken either immediately prior or subsequent to the addition of sample. Mixing of the two reagents can be accomplished either by hand to form a single working reagent, or in situ by automated analyzer. G6PD catalyzes the conversion of G6P to 6-phospho-gluconic acid (6PGA), generating the reduced coenzyme. The change in absorbance due to the re-oxidation of the in situ generated reduced coenzyme is proportional to the concentration of analyte in the sample. The unique feature of the invention is the in situ generation of reduced coenzyme, with either simultaneous or subsequent re-oxidation of coenzyme by analyte, substrate, and specific enzymes. The in situ generation of the reduced coenzyme greatly improves the stability of the reagents.

The method of the invention is easily applied to the determination of total $CO_2$ in comprising the steps of:

(a) mixing the sample with the coenzyme and enzyme substrates, and substrate specific enzymes, (b) measuring the absorbance of the solution at 320–380 nm, (c) measuring the absorbance of the solution at about 320–380 nm following an appropriate time subsequent to step (b), wherein the total $CO_2$ in the sample is proportional to the change in absorbance due to the re-oxidation of the reduced coenzyme which is generated in situ.

As mentioned previously the coenzymes and enzyme substrates may be mixed with the substrate specific enzymes prior to addition of sample, or the coenzyme and enzyme substrates may be mixed with sample and a first absorbance reading taken, after which substrate specific enzymes are added step (a) above is meant to encompass both alternatives and the first alternative is preferred.

For example, determination of total $C_{o2}$ according to the method of the invention is according to the following reaction sequence:

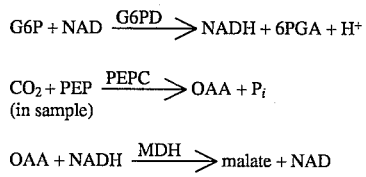

A body fluid sample such as serum or plasma is mixed with the coenzyme NAD and the enzyme substrates known to be used in the quantitation of total $CO_2$, G6P and PEP. The absorbance of the mixture is measured within a wavelength range of 320–380 nm. The enzymes are then added to this reaction mixture and a second absorbance reading is taken.

In this reaction sequence NAD is reduced to NADH due to conversion of G6P to 6PGA by G6PD. The analyte and PEP are converted into OAA and phosphate by the catalytic action of PEPC. The OAA produced is then reduced to malate by the catalytic action of MDH. The concentration of $CO_2$ in the sample is proportional to the change in absorbance due to the re-oxidation of NADH which absorbs strongly at around 340 nm or within a range of from 320–380 nm.

The appropriate time for the second absorbance measurement is preferably three minutes although a wider range is suitable such as 2–6 minutes.

The instant invention also provides for two novel reagent compositions used in the above method. The first reagent composition consists essentially of the coenzyme and enzyme substrates. This reagent [Reagent 1] is comprised of PEP, G6P, and NAD.

The second reagent composition consists essentially of the enzymes which catalyze the conversion of the substrates and generate the co-enzyme NADH. This reagent [Reagent 2] is comprised of PEPC in an amount sufficient to catalyze the conversion of PEP to OAA; G6PD in an amount sufficient to catalyze the conversion of G6P to 6PGA; MDH in an amount sufficient to catalyze the conversion of OAA to malate.

Reagents 1 and 2 may additionally contain buffers, preservatives, chelating agents, surface active agents, protease inhibitors, LDH inhibitors, antibacterials and other constituents which perform stability enhancing functions but do not materially affect the characteristics of the invention. Suitable buffers are potassium phosphate, ammonium phosphate, HEPES, 4-morpholine propanesulfonic acid (MOPS) or 2-[tris(hydroxymethyl)methylamino]-1-ethanesulfonic acid (TES). The sample to be tested may be diluted with any suitable diluent if desired, such as deionized water or saline.

Preservatives such as sodium azide (NaN3), hydroxybenzoic acid or gentamicin are suitable. Non-ionic surface active agents such as octyl phenoxypolyethoxy ethanol or a polyoxyethylene fatty alcohol ether are suitable. PMSF or Aprotinin are known protease inhibitors and, sodium oxamate, oxalic acid or gossypol will effectively inhibit interference due to Lactic Dehydrogenase. A variety of chelating agents such as EDTA, EGTA, N-(2-hydroxyethyl)ethylenediaminetriacetic acid (HEDTA), etc. are also suitable. Suitable defoaming agents may also be added if desired. Enzyme stabilizers and activators such as dithiothreitol (DTT), bovine gamma globulin (BGG), $Mg^{2+}$, N-acetyl cysteine (NAC) and glycerol may be suitable.

The instant invention also comprises a diagnostic test kit for use in determining total $C0_2$ in a sample body fluid which test kit contains:

(a) a container of reagent 1, (b) a container of reagent 2,

In the preferred embodiment, 1 to 5 microliters of serum or plasma is mixed with about 100 to 300 microliters of Reagent 1. The absorbance is read at about 340 nm. The reaction mixture is then mixed with about 20 to 94 microliters of Reagent 2 and 1–75 µl of diluent. The second absorbance reading is taken at about 340 nm and the difference in absorbance is proportional to the concentration of total $CO_2$ in the sample.

The best results are achieved when about 2 microliters of sample, about 20 microliters of a diluent such as deionized water or saline, and about 150 microliters of Reagent 1 are mixed and the absorbance of the solution is measured at about 340 nm. Then about 50 microliters of Reagent 2 and about 30 microliters of diluent are added to this reaction mixture and a second absorbance reading is taken.

It should also be noted that the order in which Reagent 1 and Reagent 2 are added to the sample may be interchanged, Namely, the sample may be first mixed with Reagent 2 and the absorbance read, after which Reagent 1 is added to the reaction mixture and a second absorbance reading taken. Alternatively, Reagents 1 & 2 may be added together, the absorbance read and a second absorbance reading taken following sample addition.

The essential constituents of Reagent 1 are PEP, G6P and NAD. Reagent 1 may additionally contain a buffer such as potassium phosphate, magnesium chloride or sulfate, and a preservative. Magnesium chloride in the form of $MgCl_2 \cdot 6H_{20}$ works well, and a preservative such as sodium azide ($NaN_3$) is suitable. Reagent 1 may also contain a chelating agent, a nonionic surface active agent, an inhibitor of LDH and a silicon based defoaming agent. The range of concentrations of the various ingredients are about 2 to 50 millimolar PEP, 1.0 to 2.0 millimolar G6P, 2 to 10 millimolar NAD, and 2 to 25 millimolar $MgCl_2$ and 0.1 to 1% $NaN_3$, 10–100 mM Potassium Phosphate, 0.1–0.5 mM EGTA, 0.01–0.1% of nonionic surface active agent and 0.1–10 mM sodium oxamate and 0.01–0.1% of a silicon based defoaming agent. In a preferred embodiment Reagent 1 should contain about 50 millimolar potassium phosphate at pH 6.9, about 6.7 millimolar $MgCl_2$, 0.1% $NaN_3$, 1.2 millimolar G6P, 8.0 millimolar NAD, 8.0 millimolar PEP, 3.3 millimolar oxamate, 0.2 millimolar EGTA, and 0.01% of a non-ionic surface active agent such as octyl phenoxy polyethoxy ethanol and 0.05% of a silicone-based defoaming agent.

Reagent 2 consists essentially of PEPC in an amount sufficient to catalyze the conversion of PEP to OAA; G6PD in an amount sufficient to catalyze the conversion of G6P to 6PGA; and MDH in an amount sufficient to catalyze the conversion of OAA to malate. Reagent 2 may additionally contain buffers and various other ingredients such as chelating agents, surface active agents, antibacterials, or preservatives, etc., for example, bovine gamma globulin (BGG), $NaN_3$, EDTA, PMSF, EGTA, and glycerol. Reagent 2 preferably contains 1000 to 2200 U/L PEPC; 5,000 to 62,000 U/L G6PD; and 2400 to 11,000 U/L MDH. Reagent 2 may further contain the following ranges of ingredients: 20 to 200 millimolar ammonium phosphate, 0.1 to 1% BGG, 1 to 30 millimolar DTT, 1 to 40% glycerol, 0.1–1% $NaN_3$, 0.1–0.5 mM EDTA and 0.1–0.5 mM PMSF. In a preferred embodiment Reagent 2 contains about 1400 U/L PEPC, 50,000 U/L G6PD, 7000 U/L MDH, 100 millimolar ammonium phosphate at PH 7.2, 20 millimolar DTT, 0.1% $NaN_3$, 30% glycerol; 0.1% BGG; 0.2 mM EDTA and 0.1 mM PMSF.

Ideally Reagents 1 and 2 should be formulated at about pH 7 to minimize the absorption of atmospheric $CO_2$. These reagents work particularly well on automated clinical chemistry analyzers such as the COBAS BIO®, COBAS FARA®, and COBAS MIRA™ (Hoffmann-La Roche Inc., Nutley, N.J.). The Reagent 2 components such as BGG, DTT, and glycerol act as enzyme stabilizers and activators. Sodium oxamate is an inhibitor of the enzyme lactate dehydrogenase and is included to prevent endogenous pyruvate, normally found in human body fluids, from interfering in the assay. Magnesium ion assists the conversion of PEP to OAA by PEPC.

The improved method of the invention is also easily applied to the determination of ammonia in a sample body fluid, and the instant invention is also directed to a method for the determination of ammonia in a sample body fluid comprising the steps of:

(a) mixing the sample with substrates specific enzymes, (b) measuring the absorbance of the solution at 320–380nm, (c) mixing the reaction mixture of step (a) with the coenzyme and enzyme substrates, (d) measuring the lowest absorbance at 320–380 nm after the coenzyme has been completely reoxidized.

wherein the concentration of ammonia in the sample is proportional to the change in absorbance due to the re-oxidation of the reduced coenzyme generated in situ.

The preferred coenzyme is $NADP^+$ in the determination of ammonia according to the instant invention. The ammonia containing sample, preferably serum, plasma or urine, is mixed with α-ketoglutarate, $NADP^+$, and G6P and a blank reading is taken. G6PD and Glutamate Dehydrogenase (G1DH) are then added to the reaction mixture causing a rapid increase in absorbance due to the formation of NADPH which absorbs strongly at about 340 nm or within a range of 320–380 nm. The absorbance then slowly decreases due to the subsequent oxidation of NADPH in the ammonia reaction:

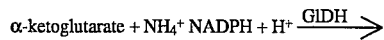
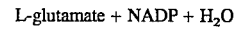

A second absorbance reading is taken at the point of lowest absorbance after the NADPH has been oxidized. The change in absorbance between the first and second reading is proportional to the concentration of ammonia in the sample.

Alternatively, Reagents 3 and 4 may be mixed first allowing the NADPH to be generated. Then sample is added.

The instant invention also comprises the novel reagent compositions used in the determination of ammonia according to the method of the invention.

The first ammonia reagent, [Reagent 3]consists essentially of $NADP^+$ and G6P. Reagent 3 may also contain MES buffer (2-[N-morpholino]ethane sulfonic acid) or other buffers or stabilizers. For example Reagent 3 may contain 50–150 mM MES buffer, pH 6.0, 10–50 mM NADP+ and 10–20 mM G6P. In a preferred embodiment Reagent 3 contains approximately:

80 mM MES buffer pH 6.0

26.4 mM $NADP^+$ 7.9 mM G6P

The second ammonia reagent [Reagent 4]consists essentially of α-ketoglutarate, G6PD and G1DH. Reagent 4 may also contain Tris (Tris(hydroxymethyl)aminomethane) buffer or other buffers or stabilizers. For example, Reagent 4 may comprise 25–500 mM Tris buffer, pH 8.0, 2–15 mM α-ketoglutarate, 5–15,000 U/L G6PD and 5–40,000 U/L GLDH. In a preferred embodiment Reagent 4 contains approximately:

320 mM Tris, pH 8.0

8,800 U/L G6PD 22,000 U/L G1DH 7.9 mM α-ketoglutarate

The determination of ammonia in a sample may be made on the COBAS MIRA in two ways. In the first, single working reagent is prepared by mixing 1 volume of Reagent 3 with 10 volumes of Reagent 4. Then 25–75 μl sample is pipetted simultaneously with 100–200 μl working reagent in the first cycle. An absorbance reading at 340 nm is taken at 4.5 sec (T1) after reaction has begun, and again at cycle 10 (∼ 4 min.) when the reaction is complete. The difference in absorbance readings correlates with the quantity of ammonia in the sample.

Rather than prepare a working reagent, another alternative is to let the COBAS MIRA pipet Reagents 3 and 4 separately in a 1:10 ratio, respectively. For example 10–20 μl Reagent 3 and 100–200 μl Reagent 4 are pipetted in the first cycle, and complete generation of NADPH is achieved by cycle 3 (as verified by a maximum $A_{340}$). Then 25–75 μl sample is pipetted in cycle 4. A final absorbance reading at 340 nm is taken 10 cycles later, and the difference in $A_{340}$ between cycles 14 and 3 is proportional to the ammonia concentration. An equally acceptable variation in the pipetting sequence is to add sample and Reagent 4 together in cycle 1, take a $A_{340}$ reading, and then add Reagent 3 in cycle 2. As before, the final $A_{340}$ is measured about 10 cycles later. This variation was used below in EXAMPLE 3.

The instant invention also comprises a diagnostic test kit for use in determining ammonia in a sample body fluid which test kit contains:

(a) a container of Reagent 3, (b) a container of Reagent 4,

The present invention will be further described in connection with the following examples which are set forth for the purposes of illustration only.

EXAMPLE 1

Reagent Preparation

Reagent 1(1 liter): 8.71 g potassium phosphate (dibasic, anhydrous), 1 g $NaN_3$, 0.076 g EGTA (acid form), 0.366 g Oxamate (Monosodium salt) are dissolved in about 950 ml deionized water. The final components are fully dissolved in the reagent solution in the following order: first, 2.8 g Phosphoenolpyruvate (Mono-cyclohexylammonium salt); second, 5.86 g $NAD.3H_{20}$ (acid form); third, 1.36 g $MgCl_2.6H_2O$; fourth, 0.34 g Glucose-6-phosphate (Monosodium Salt). Finally 0.1 g Triton X-100 (reduced) and 0.5 g Foamaster FLD are added, the pH adjusted to 6.9 with KOH, and the volume brought to 1 liter with deionized water. The concentrations of the components in Reagent 1 are: 50 mM potassium phosphate, pH 6.9, 1.2 mM G6P, 8.0 mM $NAD^+$, 8.0 mM PEP, 6.7 mM $MgCl_2$, 3.3 mM oxamate, 0.2 mM EGTA, 0.1% $NaN_3$, 0.01% Triton X-100, and 0.05% Foamaster FLD.

Reagent 2 (1 liter): 3.91 g of monobasic ammonium phosphate (anhydrous) and 8.72 g dibasic ammonium phosphate (anhydrous) are dissolved in about 650 mls deionized water along with 1 g $NaN_3$, and 0.058 g EDTA (acid form). This is mixed with 300 ml. glycerol, and the pH adjusted to 7.2 with $NH_4OH$, following which 1 g of Bovine gamma-globulin (BGG) and 3.09 g dithiothreitol (DTT) are added and dissolved. Then 50,000 units of G6PD (L. Mesenteroides), 1400 U of PEPC (Maize leaf) and 7000 units of MDH (pig heart cytosol) are added with gentle stirring, followed by addition with stirring of 1 ml of a 0.1 M solution of phenylmethylsulfonyl fluoride (PMSF) in isopropanol. The pH is adjusted to 7.2 with $NH_4OH$ if necessary, and the volume adjusted to 1 liter with deionized water. The final concentrations of the components in Reagent 2 are: 100 mM ammonium phosphate, pH 7.2, 20 mM DTT, 0.2 mM EDTA, 0.1 mM PMSF, 0.1% $NaN_3$, 30% glycerol, 50,000 U/L G6PD, 1400 U/L PEPC, and 7000 U/L MDH. The final concentration of the critical reagents in the reaction mixture are 0.72 mM G6P, 4.8 mM PEP, 4.8 mM $NAD^+$, 4.0 mM $MgCl_2$, 10,000 U/L G6PD, 280 U/L PEPC, and 1400 U/L MDH.

EXAMPLE 2

$CO_2$ Determination on the COBAS-MIRA

The assay is conducted at 37° C. 150 μl of Reagent 1, 50 μl of reagent 2, and 30 μl of diluent are mixed in the reaction cuvette and allowed to incubate for three minutes. Then, 2 μl of sample and 18 μl of diluent are added and the absorbance at 340 nm measured immediately after mixing. Three minutes later, the absorbance at 340 nm is measured a second time. The absorbance change is proportional to the concentration of $CO_2$ in the sample. Standards and controls are run in conjunction with the unknowns, and the $CO_2$ concentration in the unknown samples is calculated from the standard curve in the usual manner.

EXAMPLE 3

Ammonia determination on the COBAS MIRA

The assay is conducted at 37° C. and 130 μl of Reagent 4 is mixed with 50 μl sample in the first cycle and the absorbance is read at 340 nm. 13 μl Reagent 3 is then added and after 4 minutes (cycle 11) a second absorbance reading is made at 340 nm. From the change in absorbance between the two readings the ammonia concentrations are determined. The table below illustrates the absorbance changes when ammonia is determined according to the method of the invention:

| SAMPLE | A(cycle 1) | A(cycle 11) | ΔA(cycle 11 − cycle 1) |
|---|---|---|---|
| 50 μM std. | 0.6601 | 0.6026 | −0.0575 |
| 88 μM | 0.6568 | 0.5785 | −0.0783 |
| 132 μM | 0.6460 | 0.5455 | −0.1005 |
| 175 μM | 0.6391 | 0.5202 | −0.1188 |

A(cycle 1) is the absorbance of Reagent 4 and sample. A(cycle 11) is the absorbance after Reagent 3 was added. ΔA(cycle 11-cycle 1) is the change in absorbance due to the ammonia reaction and is used to calculate the ammonia concentration in the sample.

While the invention has been described in connection with the preferred embodiment, it is not intended to limit the scope of the invention to the particular form set forth, but, on the contrary, it is intended to cover such alternatives, modifications and equivalents as may be included within the spirit and scope of the appended claims.

We claim:

1. In an enzymatic method for determining the concentration of an analyte in a body fluid sample by measuring the change in absorbance of a reaction mixture containing said sample, the change in absorbance due to oxidation of a reduced nicotinamide coenzyme in the reaction mixture, comparing the change in absorbance with the analyte to the change in absorbance with standards which calibrate for reaction conditions and calculating the concentration of said analyte, the improvement comprising generating a reduced nicotinamide coenzeyme in situ by mixing the body fluid sample, an oxidized nicotinamide coenzyme, a substrate is a molar mount equal to or less than the molar amount of the oxidized nicotinamide coenzyme added, and an enzyme specific for said substrate, such that the reduced nicotinamide coenzyme is generated in situ from the oxidized coenzyme by reaction of said substrate with the substrate specific enzyme, the substrate specific enzyme being present in an amount such that the in situ generation of the reduced nicotinamide coenzyme occurs at a rate equal to or greater than reoxidation of the reduced coenzyme by an analyte specific enzyme.

2. In an enzymatic method for determining the concentration of an analyte in a body fluid sample by measuring the change in absorbance of a reaction mixture containing said sample, the change due to oxidation of a reduced nicotinamide coenzyme in the reaction mixture, comparing the change in absorbance with the analyte to the change in absorbance with standards which calibrate for reaction conditions and calculating the concentration of said analyte, the improvement comprising generating a reduced nicotinamide coenzyme in situ by mixing the body fluid sample, an oxidized nicotinamide coenzyme, glucose-6-phosphate in a molar amount equal to or less than the molar amount of the oxidized nicotinamide coenzyme added, and glucose-6-phosphate dehydrogenase, such that the reduced nicotinamide coenzyme is generated in situ from the oxidized coenzyme by reaction with glucose-6-phosphate and glucose-6-phosphate dehydrogenase, the glucose-6-phosphate dehydrogenase being present in an amount such that the in situ generation of the reduced nicotinamide coenzyme occurs at a rate equal to or greater than reoxidation of the reduced coenzyme by an analyte specific enzyme.

3. The method of claim 2 wherein the coenzyme is selected from the group consisting of nicotinamide adenine dinucleotide and nicotinamide adenine dinucleotide phosphate.

4. The method of claim 2 wherein the sample body fluid is serum, plasma or urine.

5. The method of claim 2 wherein the analyte is selected from the group consisting of carbon dioxide and ammonia.

6. A method for the determination of total $CO_2$ in a sample body fluid comprising the steps of:
   (a) mixing phosphoenolpyruvate, phosphoenolpyruvate carboxylase, malate dehydrogenase, an oxidized nicotinamide coenzyme, an enzyme substrate, and an enzyme specific for said substrate to produce a determination mixture, wherein the reaction of said enzyme and substrate with the oxidized nicotinamide coenzyme generates reduced coenzyme, in situ;
   b) adding the sample to said determination mixture to produce a reaction mixture;
   c) measuring the absorbance of said determination mixture immediately before step (b) or said reaction mixture immediately subsequent to step (b) at 320–380 nanometers (nm);
   d) measuring the absorbance of said reaction mixture after step (c) at 320–380 nm after all or part of the reduced coenzyme has been reoxidized at a time such that an observed absorbance change is correlatable to the concentration of $CO_2$ when compared to the change in absorbance with standards which calibrate for reaction conditions; and
   e) determining the concentration of $CO_2$ in the sample as calculated by comparison to said calibration standards.

7. The method of claim 6 wherein the sample body fluid is serum, plasma or urine.

8. The method of claim 6 wherein the substrate is glucose-6-phosphate which is in a molar amount equal to or less than the molar amount of oxidized nicotinamide coenzyme added, and the enzyme is glucose-6-phosphate dehydrogenase which is in an amount such that the formation of reduced nicotinamide coenzyme is complete when the absorbance is measured in step (c).

9. The method of claim 6 wherein in step (a) the oxidized nicotinamide coenzyme is nicotinamide adenine dinucleotide and the concentration of nicotinamide adenine dinucleotide is from about 2 mM to about 10 mM, and wherein the concentration of phosphoenolpyruvate is from about 2 mM to about 50 mM, the enzyme substrate is glucose-6-phosphate and the concentration of glucose-6-phosphate is from about 1 mM to about 2 mM, the concentration of phosphoenolpyruvate carboxylase is from about 1,000 U/L to about 2,200 U/L, the enzyme specific for said substrate is glucose-6-phosphate dehydrogenase and the concentration of glucose-6-phosphate dehydrogenase is from about 5,000 U/L to about 62,000 U/L, and the concentration of malate dehydrogenase is from about 2,400 U/L to about 11,000 U/L.

10. The method of claim 9 wherein the concentration of nicotinamide adenine dinucleotide is about 4.8 mM, the concentration of phosphoenolpyruvate is about 4.8 mM, the concentration of glucose-6-phosphate is about 0.72 mM, the concentration of phosphoenolpyruvate carboxylase is about 280 U/L, the concentration of glucose-6-phosphate dehydrogenase is about 10,000 U/L, and the concentration of malate dehydrogenase is about 1,400 U/L.

11. A method for the determination of total $CO_2$ in a sample body fluid comprising the steps of:
   (a) mixing the sample with phosphoenolpyruvate, an oxidized nicotinamide coenzyme and a substrate to produce a determination mixture, wherein said substrate reacts with an enzyme specific for said substrate with the oxidized coenzyme to generate reduced coenzyme in situ;
   b) adding to said determination mixture phosphoenolpyruvate carboxylase, malate dehydrogenase and said enzyme specific for said substrate to produce a reaction mixture;
   c) measuring the absorbance of said determination mixture immediately before step (b) or said reaction mixture immediately subsequent to step (b) at 320–380 nanometers (nm);
   d) measuring the absorbance of said reaction mixture after step (c) at 320–380 nm after all or part of the reduced coenzyme has been reoxidized at a time such that the observed absorbance change is correlatable to the concentration of $CO_2$ when compared to the change in absorbance with standards which calibrate for reaction conditions; and
   e) determining the concentration of $CO_2$ in the sample as calculated by comparison to said calibration standards.

12. The method of claim 11 wherein the oxidized nicotinamide coenzyme is nicotinamide adenine dinucleotide, the substrate is glucose-6-phosphate which is in a molar amount equal to or less than the molar amount of nicotinamide adenine dinucleotide added, and the enzyme is glucose-6-phosphate dehydrogenase which is in an amount such that the rate of generation of the reduced nicotinamide coenzyme is equal to or greater than the rate of reoxidation of the reduced nicotinamide coenzyme.

13. A method for the determination of total $CO_2$ in a sample body fluid comprising the steps of:
   (a) mixing the sample with phosphoenolpyruvate carboxylase, malate dehydrogenase and an enzyme specific for a substrate to produce a determination mixture, wherein the reaction of said enzyme and substrate with an oxidized nicotinamide coenzyme generates reduced nicotinamide coenzyme in situ;
   b) adding to said determination mixture phosphoenolpyruvate, the oxidized nicotinamide coenzyme, and said substrate to produce a reaction mixture;
   c) measuring the absorbance of said determination mixture immediately before step (b) or said reaction mixture immediately subsequent to step (b) at 320–380 nanometers (nm);
   d) measuring the absorbance of said reaction mixture after step (c) at 320–380 ran after all or pan of the reduced coenzyme has been reoxidized at such time that the observed absorbance change is correlatable to the concentration of CO2 when compared to the change in absorbance with standards which calibrate for reaction conditions; and
   e) determining the concentration of $CO_2$ in the sample as calculated by comparison to said calibration standards.

14. The method of claim 13 wherein the oxidized nicotinamide coenzyme is nicotinamide adenine dinucleotide, the substrate is glucose-6-phosphate which is in a molar amount equal to or less than the molar amount of nicotinamide adenine dinucleotide added, and the enzyme is glucose-6-phosphate dehydrogenase which is in an amount such that the rate of formation of the reduced nicotinamide coenzyme me is equal to or greater than the rate of reoxidation of the reduced nicotinamide coenzyme.

15. A diagnostic test kit for an enzymatic method for determining total $CO_2$ in a sample body fluid by measuring the change in absorbance of a reaction mixture containing said sample, the change in absorbance due to oxidation of reduced nicotinamide adenine dinucleotide in the reaction mixture, comparing the change in absorbance to the change in absorbance with standards which calibrate for reaction conditions and calculating the concentration of $CO_2$, comprising:

a) a container of a first reagent comprising phosphoenolpyruvate, nicotinamide adenine dinucleotide and glucose-6-phosphate which is in a molar amount equal to or less than the molar amount of nicotinamide adenine dinucleotide added; and b) a container of a second reagent comprising phosphoenolpyruvate carboxylase which is in an amount sufficient to catalyze the conversion of phosphoenolpyruvate and $CO_2$ in the sample to oxaloacetic acid and inorganic phosphate, malate dehydrogenase which is in an amount sufficient to catalyze the conversion of oxaloacetic acid and reduced nicotinamide adenine dinucleotide to malate and oxidized nicotinamide adenine dinucleotide at a rate equal to or greater than tile conversion of phosphoenolpyruvate to oxaloacetic acid, and glucose-6-phosphate dehydrogenase which is in an amount sufficient to catalyze the conversion of glucose-6-phosphate mad oxidized nicotinamide adenine dinucleotide to 6-phosphogluconate and reduced nicotinamide adenine dinucleotide such that the rate of conversion of glucose-6-phosphate to 6-phosphogluconate is equal to or greater than the rate of conversion of oxaloacetic acid and reduced nicotinamide adenine dinucleotide to malate and oxidized nicotinamide adenine dinucleotide.

16. The kit of claim 15 wherein the concentration of nicotinamide adenine dinucleotide is from about 2 mM to about 10 mM, the concentration of phosphoenolpyruvate is from about 2 mM to about 50 mM, the concentration of glucose-6-phosphate is from about 1 mM to about 2 mM, the concentration of phosphoenolpyruvate carboxylase is from about 1,000 U/L to about 2,200 U/L, the concentration of glucose-6-phosphate dehydrogenase is from about 5,000 U/L to about 62,000 U/L, and the concentration of malate dehydrogenase is from about 2,400 U/L to about 11,000 U/L.

17. The kit of claim 16 wherein the concentration of nicotinamide adenine dinucleotide is about 8.0 mM, the concentration of phosphoenolpyruvate is about 8.0 mM, the concentration of glucose-6-phosphate is about 1.2 mM, the concentration of phosphoenolpyruvate carboxylase is about 1,400 U/L, the concentration of glucose-6-phosphate dehydrogenase is about 50,000 U/L, and the concentration of malate dehydrogenase is about 7,000 U/L.

18. A method for the determination of ammonia in a sample body fluid comprising the steps of:

(a) mixing α-ketoglutarate, glutamate dehydrogenase, an oxidized nicotinamide coenzyme, an enzyme substrate, and an enzyme specific for said substrate to produce a determination mixture, wherein the reaction of said enzyme and said substrate with the oxidized nicotinamide coenzyme generates reduced coenzyme in situ;

b) adding the sample to said determination mixture to produce a reaction mixture;

c) measuring the absorbance of said determination mixture immediately before step (b) or said reaction mixture immediately subsequent to step (b) at 320–380 nanometers (nm);

d) measuring the absorbance of said reaction mixture after step (c) at 320–380 nm after all or part of the reduced coenzyme has been reoxidized at a time such that an observed absorbance change is correlatable to the concentration of ammonia when compared to the change in absorbance with standards which calibrate for reaction conditions; and e) determining the concentration of ammonia in the sample as calculated by comparison to said calibration standards.

19. The method of claim 18 wherein the sample body fluid is sermon, plasma or urine.

20. The method of claim 18 wherein the substrate is glucose-6-phosphate which is in a molar amount equal to or less than the molar amount of oxidized nicotinamide coenzyme added, and the enzyme is glucose-6-phosphate dehydrogenase which is in an amount such that the generation of reduced nicotinamide coenzyme is complete when the absorbance is measured in step (c).

21. The method of claim 18 wherein the coenzyme is nicotinamide adenine dinucleotide phosphate and wherein the concentration of nicotinamide adenine dinucleotide phosphate is from about 10 mM to about 50 mM, the enzyme substrate is glucose-6-phosphate and the concentration of glucose-6-phosphate is from about 10 mM to about 20 mM, the enzyme specific for said substrate is glucose-6-phosphate dehydrogenase and the concentration of glucose-6-phosphate dehydrogenase is from about 5 U/L, to about 15,000 U/L, the concentration of glutamate dehydrogenase is from about 5 U/L to about 40,000 U/L and the concentration of α-ketoglutarate is from about 2 mM to about 15 mM.

22. The method of claim 21 wherein the concentration of nicotinamide adenine dinucleotide phosphate is about 26.4 mM, the concentration of glucose-6-phosphate is about 7.9 mM, the concentration of glucose-6-phosphate dehydrogenase is about 8,800 U/L, the concentration of glutamate dehydrogenase is about 22,000 U/L, and the concentration of α-ketoglutarate is about 7.9 mM.

23. A method for the determination of ammonia in a sample body fluid comprising the steps of:

(a) mixing the sample with α-ketoglutarate, glutamate dehydrogenase and an enzyme specific for a substrate to produce a determination mixture, wherein the reaction of said substrate and said enzyme with an oxidized nicotinamide coenzyme generates reduced nicotinamide coenzyme in situ;

b) adding to the determination mixture said oxidized nicotinamide coenzyme and said substrate to produce a reaction mixture;

c) measuring the absorbance of said determination mixture immediately before step (b) or said reaction mixture immediately subsequent to step (b) at 320–380 nanometers (nm);

d) measuring the absorbance of said reaction mixture after step (c) at 320–380 nm after all or part of the reduced coenzyme has been reoxidized at such time that the observed absorbance change is correlatable to the concentration of ammonia when compared to the change in absorbance with standards which calibrate for reaction conditions; and e) determining the concentration of ammonia in the sample as calculated by comparison to said calibration standards.

24. The method of claim 23 wherein the coenzyme is nicotinamide adenine dinucleotide phosphate, the substrate is glucose-6-phosphate which is in a molar amount equal to or less than the molar amount of nicotinamide adenine dinucleotide phosphate added, and the enzyme is glucose-6-phosphate dehydrogenase which is in an amount such that the rate of generation of reduced nicotinamide coenzyme is equal to or greater than the rate of oxidation of the reduced nicotinamide coenzyme.

25. A diagnostic test kit for an enzymatic method for determining ammonia in a sample body fluid by measuring the change in absorbance of a reaction mixture containing said sample, the change in absorbance due to oxidation of reduced nicotinamide adenine dinucleotide phosphate in the reaction mixture, comparing the change in absorbance to the change in absorbance with standards which calibrate for reaction conditions and calculating the concentration of ammonia, comprising:

a) a container of a first reagent comprising nicotinamide adenine dinucleotide phosphate and glucose-6-phosphate which is in a molar amount equal to or less than the molar amount of nicotinamide adenine dinucleotide phosphate added; and b) a container of a second reagent comprising $\alpha$-ketoglutarate, glutamate dehydrogenase and glucose-6-phosphate dehydrogenase which is in an amount sufficient to catalyze the conversion of glucose-6-phosphate to 6-phosphogluconate such that the rate of conversion of glucose-6-phosphate to 6-phosphogluconate is equal to or greater than the rate of conversion of $\alpha$-ketoglutarate and ammonia to L-glutamate.

26. The kit of claim 25 wherein the concentration of nicotinamide adenine dinucleotide phosphate is from about 10 mM to about 50 mM, the concentration of glucose-6-phosphate is from about 10 mM to about 20 mM, the concentration of glucose-6-phosphate dehydrogenase is from about 5 U/L to about 15,000 U/L, the concentration of glutamate dehydrogenase is from about 5 U/L to about 40,000 U/L, and the concentration of $\alpha$-ketoglutarate is from about 2 mM to about 15 mM.

27. The kit of claim 26 wherein the concentration of nicotinamide adenine dinucleotide phosphate is about 26.4 mM, the concentration of glucose-6-phosphate is about 7.9 mM, the concentration of glucose-6-phosphate dehydrogenase is about 8,800 U/L, the concentration of glutamate dehydrogenase is about 22,000 U/L, and the concentration of $\alpha$ketoglutarate is about 7.9 mM.

* * * * *

UNITED STATES PATENT AND TRADEMARK OFFICE
CERTIFICATE OF CORRECTION

PATENT NO. : 5,589,348

DATED : December 31, 1996

INVENTOR(S) : Richard A. Kaufman, John M. Konopka, Henry J. Rosenfeld, Janine E. Sabo It is certified that error appears in the above-identified patent and that said Letters Patent is hereby corrected as shown below:

In claim 1, column 8, line 37, delete "mount" and insert -- amount --.

In claim 1, column 8, line 35, delete "coenzeyme" and insert -- coenzyme --.

In claim 1, column 8, line 36, delete "a substrate is a" and insert "a substrate in a".

In claim 13, column 10, line 48, delete "ran" and insert --nm --; and delete "pan" and insert -- part --.

In claim 13, column 10, line 51, delete "CO2" and insert -- $CO_2$ --.

In claim 14, column 10, line 63, delete "me".

In claim 15, column 11, line 21, delete "tile" and insert -- the --.

In claim 15, column 11, line 24, delete "mad" and insert "and".

In claim 19, column 12, line 10, delete "sermon" and insert -- serum --.

In claim 21, column 12, line 26, delete the "," after "5 U/L".

UNITED STATES PATENT AND TRADEMARK OFFICE
CERTIFICATE OF CORRECTION

PATENT NO. : 5,589,348
DATED : December 31, 1996
INVENTOR(S) : Richard A. Kaufman, et. al.

It is certified that error appears in the above-indentified patent and that said Letters Patent is hereby corrected as shown below:

In claim 27, column 14, line, delete " αketoglutarate" and insert -- α-ketoglutarate --.

Signed and Sealed this

Twenty-third Day of September, 1997

Attest:

BRUCE LEHMAN

Attesting Officer

Commissioner of Patents and Trademarks